(12) United States Patent
Rattan

(10) Patent No.: US 7,504,419 B2
(45) Date of Patent: Mar. 17, 2009

(54) DIASTEREOMERS OF 4-ARYLOXY-3-HYDROXYPIPERIDINES

(76) Inventor: Balvinder Singh Rattan, 19 Nutter Lane, Wanstead, E11 2HZ London (GB)

( * ) Notice: Subject to any disclaimer, the term of this patent is extended or adjusted under 35 U.S.C. 154(b) by 427 days.

(21) Appl. No.: 10/932,857

(22) Filed: Sep. 2, 2004

(65) Prior Publication Data

US 2005/0203136 A1    Sep. 15, 2005

Related U.S. Application Data

(60) Provisional application No. 60/502,157, filed on Sep. 10, 2003.

(51) Int. Cl.
*A61K 31/445* (2006.01)
*C07D 211/52* (2006.01)

(52) U.S. Cl. ............ 514/328; 546/219

(58) Field of Classification Search ......... 546/206, 546/219, 220; 514/328
See application file for complete search history.

(56) References Cited

U.S. PATENT DOCUMENTS 4,160,837 A    7/1979    Paioni .............. 546/220

OTHER PUBLICATIONS

Exhibit I listing of 14 CAS references.*
Xue et al. "Asymmetric synthesis . . . " J. Org. chem. v.67, p. 865-870 (2002).*
Exhibit II "tartaric Acid".*
Exhibit III "Ifexetine".*
Waldmeier et al. "Ifoxetine . . . " CA 106:12769 (1986).*
Paioni "Perhydroaza . . . " CA 88:152446 (1978).*
Davankov "Separation of enantiomeric compounds . . . " Chromatographia v.27, No. 9/10, p. 475-482 (1999).*
Husain et al. "High Performance liquid chrom . . . " Process control and quality v.10, p. 41-57 (1997).*
International Search Report for PCT/IB2004/003442.
Baker et al., Stereochemistry and Drug Efficacy and Development: Relevance of Chirality to Antidepressant and Antipsychotic Drugs, Annals of Medicine, vol. 34, 2002, pp. 537-543.
Paioni et al., Ifoxetine Sulfate, Drugs of the Future, vol. 12, No. 2, 1987, pp. 126-128.
Waldmeier et al., Ifoxetine, a compound with atypical effects on serotonin uptake, European Journal of Pharmacology, vol. 130, 1986, pp. 1-10.

* cited by examiner

*Primary Examiner*—Celia Chang
(74) *Attorney, Agent, or Firm*—Kenyon & Kenyon LLP

(57) ABSTRACT

The present invention relates to essentially pure diastereomers of 4-aryloxy-3-hydroxypiperidines, including purified diastereomers of ifoxetine, methods of purifying said diastereomers, pharmaceutical compositions comprising said diastereomers and methods of treatment utilizing said pharmaceutical compositions.

14 Claims, No Drawings

DIASTEREOMERS OF 4-ARYLOXY-3-HYDROXYPIPERIDINES

This application claims the benefit of U.S. Ser. No. 60/502,157, filed Sep. 10, 2003, herein incorporated by reference in its entirety.

FIELD OF THE INVENTION

The present invention relates to essentially pure diastereomers of 4-aryloxy-3-hydroxypiperidines, including purified diastereomers of ifoxetine, methods of purifying said diastereomers, pharmaceutical compositions comprising said diastereomers and methods of treatment utilizing said pharmaceutical compositions.

BACKGROUND OF THE INVENTION

Chemically ifoxetine is (+/−)-bis-[cis-3-hydroxy-4-(2,3-dimethyl-phenoxy)]-piperidine sulfate. According to the prior art, ifoxetine specifically and selectively blocks 5-HT reuptake in the brain without affecting the 5-HT uptake processes in the periphery (blood platelets). See Delini-Stula et al., Int Clin Psychopharmacol. 1987 July; 2 (3):201-15, herein incorporated by reference in its entirety. The prior art also states that ifoxetine displays weak or no interactions with $5-HT_1$, $5-HT_2$, $alpha_1$, $alpha_2$, beta-noradrenoceptors, histamine $H_1$, muscarinic acetylcholine, opiate, $GABA_A$, and benzodiazepine receptors in vitro, and with dopamine and $5-HT_2$ receptors in vivo. See Waldmeier et al., Eur J. Pharmacol. 1986 Oct. 14;130(1-2):1-10, herein incorporated by reference in its entirety ("Waldmeier").

The synthesis of ifoxetine is disclosed in U.S. Pat. No. 4,160,837 ("Paioni"), herein incorporated by reference in its entirety. Specifically, Paioni disclosed that that certain 4-aryloxy-3-hydroxypiperidines (1), where Ar is a substituted or unsubstituted aromatic hydrocarbon group and R is hydrogen or methyl, possess valuable pharmacological properties, and can be used for the treatment of mental depression. See also Paioni and Waldmeier 1985, Proc. VIIth Int. Symp. Medicinal Chemistry (August 27-31, Uppsala, Sweden Vol. 2, eds. Dahlbom et al., Swedish Pharmaceutical Press, Stockholm, pp. 130-132, herein incorporated by reference in its entirety.

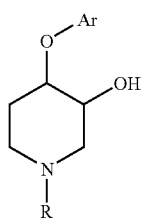

1

Specific embodiments described in Paioni were the dimethylphenoxypiperidines which included compounds 2-5. (Ifoxetine is racemic composition comprising the two cis diastereomers of compound 2.)

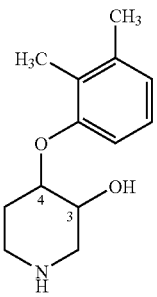

2

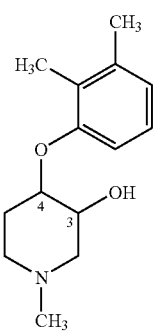

3

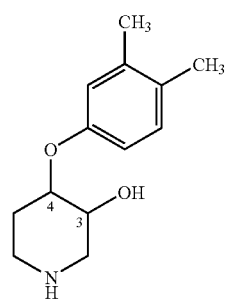

4

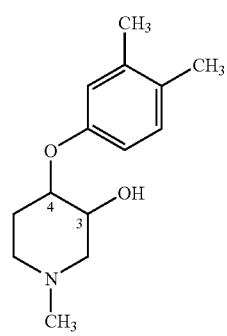

5

Since each of compounds 2-5 contains chiral centers at carbon 3 and carbon 4, the compounds comprise four possible diastereomers. For example the possible diastereomers of compound 2 comprise the following isomers which are shown below: 2a, (3S,4R), 2b (3R,4S), 2 c (3R,4R) and 2d (3S,4S).

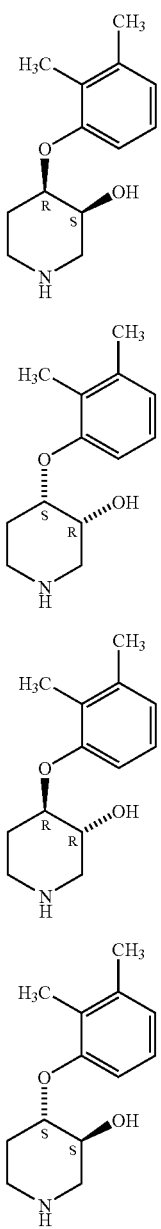

According to Paioni and Waldmeier et al, see supra, stereochemistry has little effect on the activity of compound 2.

The following U.S. patents and publications describe methods, compositions, or compounds, which comprise ifoxetine. U.S. Pat. No. 6,528,521, herein incorporated by reference in its entirety, describes a method for treating sexual dysfunction that is caused by anti-depressant medication in a patient in need of such treatment, comprising administering a therapeutically effective amount of apomorphine or a pharmaceutically acceptable salt thereof, to said patient, is disclosed. The method may be utilized for patients taking antidepressants such as tricyclic anti-depressants, monamine oxidase inhibitors or serotonin selective reuptake inhibitors (SSRI). The serotonin selective reuptake inhibitors may include ifoxetine.

U.S. Pat. No. 6,495,154, herein incorporated by reference in its entirety, describes a method for delaying the onset of ejaculation in an individual. The method involves systemic and on demand administration to an individual of a pharmaceutical formulation containing an amount of an active agent selected from the group consisting of clomipramine and pharmacologically acceptable acid addition salts thereof. Drug delivery may be accomplished via any route designed to provide systemic levels of the active agent effective to delay the onset of ejaculation. Pharmaceutical formulations and dosage forms are provided as well. In one embodiment, the pharmaceutical formulation also comprises ifoxetine.

U.S. Pat. No. 6,403,597, herein incorporated by reference in its entirety, describes a method for treatment of premature ejaculation by administration of a phosphodiesterase inhibitor, e.g., an inhibitor of a Type III, Type IV, or Type V phosphodiesterase. In a preferred embodiment, administration is on as "as needed" basis, i.e., the drug is administered immediately or several hours prior to sexual activity. Pharmaceutical formulations and packaged kits are also provided. In one embodiment, the pharmaceutical formulation also comprises ifoxetine.

U.S. Pat. Nos. 6,331,289, 6,264,917 and 6,261,537, herein incorporated by reference in their entirety, disclose targetable diagnostic and/or therapeutically active agents, e.g. ultrasound contrast agents, comprising a suspension in an aqueous carrier liquid of a reporter comprising gas-containing or gas-generating material, said agent being capable of forming at least two types of binding pairs with a target. The disclosed compositions and methods may further comprise ifoxetine.

U.S. Pat. No. 6,303,595, herein incorporated by reference in its entirety, describes a method for treating sleep apneas utilizing mirtazapine. Optionally, mirtazapine is combined with an SSRI such as fluoxetine or ifoxetine.

U.S. Pat. Nos. 6,228,864 and 5,922,341, herein incorporated by reference in their entirety, describes methods for delaying the onset of ejaculation in an individual. The methods preferably involve administration of an antidepressant drug, a serotonin agonist or antagonist, an adrenergic agonist or antagonist, an adrenergic neurone blocker, or a derivative analog thereof, within the context of an effective dosing regimen. The preferred mode of administration is transurethral; however, the selected active agent may also be delivered via intracavernosal injection or using alternative routes. Pharmaceutical formulations and kits are provided as well.

U.S. Pat. No. 5,977,099, herein incorporated by reference in its entirety, describes a pharmaceutical composition comprising mirtazapine, a SSRI and pharmaceutically acceptable auxiliaries. In particular the SSRI is selected from fluoxetine, fluvoxamine, citalopram, cericlamine, femoxetine, sertraline, paroxetine, ifoxetine, cyanodothiepin and litoxetine. The composition, which can be used to treat depressant patients has less side effects than treatment of the patients with mirtazapine or the SSRI alone.

EP Patent No. 835660, herein incorporated by reference in its entirety, describes products containing methylcobalamin in an overdose corresponding to a weekly intramuscular dose higher than 1000 micrograms, preferably higher than 1200 micrograms and corresponding more preferably to a weekly intramuscular dose of at least 1500 micrograms, and an antidepressant enhancing the serotonin level as a combined preparation for simultaneous, separate or sequential use in the treatment of multiple sclerosis or other demyelinating conditions. In one embodiment the 1 product comprises ifoxetine.

International application WO9200103, herein incorporated by reference in its entirety, describes a pharmaceutical product comprising two or three active ingredients as a combined preparation for simultaneous, separate or sequential use in therapy of depression and/or migraine. In one embodiment the pharmaceutical product comprises ifoxetine.

International application WO9200103, herein incorporated by reference in its entirety, describes prodrugs of antidepressants and the use of these prodrugs in a method for therapy and to pharmaceutical compositions comprising the prodrugs of the invention.

SUMMARY OF THE INVENTION

The present invention provides for compounds, which are essentially pure diastereomers of 4-aryloxy-3-hydroxypiperidines (1) or an addition salt thereof,

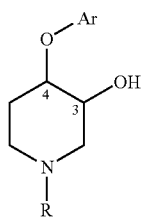

where Ar is a substituted or unsubstituted aromatic hydrocarbon group and R is hydrogen or methyl, carbon 3 is either in the R or the S configuration and carbon 4 is either in the R or the S configuration.

In a further embodiment the present invention provides for pharmaceutical compositions which comprise a pharmaceutically acceptable carrier and a compound, wherein the compound is an essentially pure diastereomers of a 4-aryloxy-3-hydroxypiperidines (1) or an addition salt thereof,

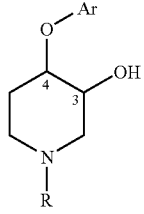

where Ar is a substituted or unsubstituted aromatic hydrocarbon group and R is hydrogen or methyl, carbon 3 is either in the R or the S configuration and carbon 4 is either in the R or the S configuration.

In a further embodiment the present invention provides for a method of treating afflictions of the central and peripheral nervous systems by administering pharmaceutical composition which comprise a pharmaceutically acceptable carrier and a compound, wherein the compounds is an essentially pure diastereomers of a 4-aryloxy-3-hydroxypiperidines (1) or an addition salt thereof,

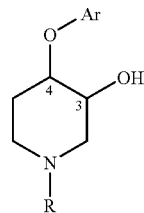

where Ar is a substituted or unsubstituted aromatic hydrocarbon group and R is hydrogen or methyl, carbon 3 is either in the R or the S configuration and carbon 4 is either in the R or the S configuration.

In a further embodiment the present invention provides for a method of binding 5-HT receptors in an animal by the administration to an animal of a pharmaceutical composition comprising a pharmaceutically acceptable carrier and a compound, wherein the compound is an essentially pure diastereomers of a 4-aryloxy-3-hydroxypiperidines (1) or an addition salt thereof,

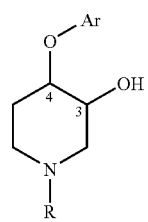

where Ar is a substituted or unsubstituted aromatic hydrocarbon group and R is hydrogen or methyl, carbon 3 is either in the R or the S configuration and carbon 4 is either in the R or the S configuration.

In a further embodiment the present invention provides for a method of purification of an essentially pure diastereomer of a 4-aryloxy-3-hydroxypiperidines (1) or an addition salt thereof,

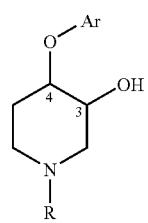

where Ar is a substituted or unsubstituted aromatic hydrocarbon group and R is hydrogen or methyl, carbon 3 is either in the R or the S configuration and the chiral center at carbon 4 is either in the R or the S configuration.

In a further embodiment the present invention provides for essentially pure (3R,4S)-4-(2,3-dimethylphenyl)-3-hydroxypiperidine or an addition salt thereof.

In a further embodiment the present invention provides for essentially pure (3S,4R)-4-(2,3-dimethylphenyl)-3-hydroxypiperidine or an addition salt thereof.

In a further embodiment the present invention provides for essentially pure (3R,4R)-4-(2,3-dimethylphenyl)-3-hydroxypiperidine or an addition salt thereof.

In a further embodiment the present invention provides for essentially pure (3S,4S)-4-(2,3-dimethylphenyl)-3-hydroxypiperidine or an addition salt thereof.

In a further embodiment the present invention provides for a pharmaceutical composition comprising essentially pure (3R,4S)-4-(2,3-dimethylphenyl)-3-hydroxypiperidine or an addition salt thereof and a pharmaceutically acceptable carrier.

In a further embodiment the present invention provides for a pharmaceutical composition comprising essentially pure (3S,4R), -4-(2,3-dimethylphenyl)-3-hydroxypiperidine or an addition salt thereof and a pharmaceutically acceptable carrier.

In a further embodiment the present invention provides for a pharmaceutical composition comprising essentially pure (3R,4R)-4-(2,3-dimethylphenyl)-3-hydroxypiperidine or an addition salt thereof and a pharmaceutically acceptable carrier.

In a further embodiment the present invention provides for a pharmaceutical composition comprising essentially pure (3S,4S)-4-(2,3-dimethylphenyl)-3-hydroxypiperidine or an addition salt thereof and a pharmaceutically acceptable carrier.

DETAILED DESCRIPTION OF THE INVENTION

We have now unexpectedly found that there are significant differences between the diastereomers of 4-aryloxy-3-hydroxypiperidines of formula (1), in their interactions with certain pharmacologically significant protein receptor sites.

As used herein the cis racemic composition refers to an unresolved mixture of cis diastereomers. As used herein the trans racemic composition refers to an unresolved mixture of trans diastereomers.

As used herein an "essentially pure diastereomer" preferably refers to a diastereomer, which is greater than about 70% pure. More preferably, "essentially pure diastereomer" refers to a diastereomer, which is greater than about 90% pure. Even more preferably, "essentially pure diastereomer" refers to a diastereomer, which is greater than about 95% pure. Most preferably, "essentially pure diastereomer" refers to a diastereomer, which is greater than about 98% pure.

As used herein an "addition salt" preferably refers to a salt of a compound of formula I prepared by reaction of a compound of formula I with a mineral or organic acid. For exemplification of pharmaceutical acid addition salts see, e.g., Berge, S. M, Bighley, L. D., and Monkhouse, D. C., J. Pharm. Sci., 66:1, 1977, incorporated by reference in its entirety. Acids commonly employed to form addition salts are inorganic acids such as hydrochloric acid, hydrobromic acid, hydroiodic acid, sulfuric acid, phosphoric acid, and the like, and organic acids such as p-toluenesulfonic, methanesulfonic acid, ethanesulfonic acid, oxalic acid, p-bromophenylsulfonic acid, carbonic acid, succinic acid, citric acid, tartaric acid, benzoic acid, acetic acid, and the like.

As used herein "pharmaceutically acceptable salts" include but are not limited to, those derived from organic acids such as acetic acid, malic acid, tartaric acid, citric acid, lactic acid, succinic acid, fumaric acid, maleic acid, oxalic acid, benzoic acid, salicylic acid, phenylacetic acid, mandelic acid, methanesulfonic acid, benzenesulphonic acid and p-toluenesulfonic acid, mineral acids such as hydrochloric and sulfuric acid and the like.

Salts may be prepared in a conventional manner by methods well-known in the art. The compounds of this invention may also exist in solvated or hydrated or polymorphic forms.

The synthesis of compositions comprising cis and trans racemate of 4-aryloxy-3-hydroxypiperidines (1) has been described by Paioni.

Purified Diastereomers of the Invention

Accordingly, the present invention provides for compounds, which are essentially pure diastereomers of 4-aryloxy-3-hydroxypiperidines (1) or an addition salt thereof,

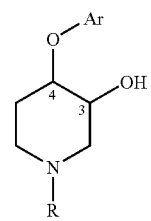

where Ar is a substituted or unsubstituted aromatic hydrocarbon group and R is hydrogen or methyl, carbon 3 is either in the R or the S configuration and carbon 4 is either in the R or the S configuration.

As used herein, "a substituted or unsubstituted aromatic hydrocarbon group" preferably refers to a substituted or unsubstituted phenyl group. Preferably a substituted phenyl group is a mono, di or tri substituted phenyl group.

Substituents of the phenyl group may be independently selected from preferably C1 to C6 alkyl, C1 to C6 alkoxy, hydroxyl or halo groups. Preferably the substituents are methyl groups.

Most preferably, Ar is selected from the group consisting of 2,3-dimethylphenyl and 3,4-dimethylphenyl.

Preferably, R is selected from the group consisting of hydrogen and methyl.

In a further embodiment the present invention provides for essentially pure (3R,4S)-4-(2,3-dimethylphenyl)-3-hydroxypiperidine or an addition salt thereof.

In a further embodiment the present invention provides for essentially pure (3S,4R)-4-(2,3-dimethylphenyl)-3-hydroxypiperidine or an addition salt thereof.

In a further embodiment the present invention provides for essentially pure (3R,4R)-4-(2,3-dimethylphenyl)-3-hydroxypiperidine or an addition salt thereof.

In a further embodiment the present invention provides for essentially pure (3S,4S)-4-(2,3-dimethylphenyl)-3-hydroxypiperidine or an addition salt thereof.

Method of Purification

Paioni does not resolve the cis and trans racemic compositions into the individual diastereomers.

Accordingly, a further embodiment the present invention provides for a method of purification of an essentially pure diastereomers of a 4-aryloxy-3-hydroxypiperidines (1) or an addition salt thereof,

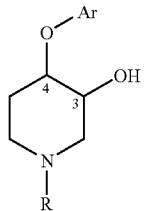

where Ar is a substituted or unsubstituted aromatic hydrocarbon group and R is hydrogen or methyl, carbon 3 is either in the R or the S configuration and the chiral center at carbon 4 is either in the R or the S configuration.

Preferably, the essentially pure diastereomers are purified from a cis racemic composition or a trans racemic composition by column chromatography. In a preferred embodiment the diastereomers are purified by HPLC. Preferably the stationary phase of the HPLC column comprises a chiral column prepared by coating silica with a chiral molecule. A preferred chiral molecule is chiral polymer such as amylose. Preferably, the hydroxyl groups on the amylose are functionalized by reacting with an isocyanate to give the corresponding carbamate. The chirality arises from the stereogenic sites on the amylose rings. Commercially available columns, which would be useful for purifying the diastereomers, include for example, CHIRALPAK® AD™. Preferably, the mobile phase comprises a polar solvent or mixtures of polar solvents. Preferred polar solvents include water, acetonitrile, methanol, or ethanol or mixtures thereof. Most preferably the mobile phase is HPLC grade ethanol. As used herein, HPLC grade ethanol preferable refers to ethanol, which is greater than about 95% pure. More preferably, HPLC grade ethanol refers to ethanol, which is greater than about 97% pure. Most preferably, HPLC grade ethanol refers to ethanol, which is greater than about 98% pure.

The temperature of the HPLC column during purification may range from about 5 to about 40° C. Most preferably the temperature range is about 20 to about 23° C. (ambient temperature).

Methods of Treatment

In a further embodiment the present invention provides for a method of treating afflictions of the central and peripheral nervous systems by administering a pharmaceutical compositions which comprise a compound, wherein the compound is an essentially pure diastereomer of a 4-aryloxy-3-hydroxypiperidine (1) or an addition salt thereof,

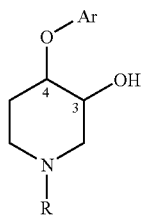

where Ar is a substituted or unsubstituted aromatic hydrocarbon group and R is hydrogen or methyl, carbon 3 is either in the R or the S configuration and carbon 4 is either in the R or the S configuration.

In particular, compositions comprising essentially pure diastereomer of the present invention are expected to be an improvement on many existing treatments for anxiety, depressive and related disorders in terms of side effect profiles, ease of dosing, patient compliance and clinical efficacy. Particular indications are for use of the essentially pure diastereomer in the treatment of: all depressive symptoms and disorders including major depression, minor depression, atypical depression, recurrent depression, dysthymia, depressive phase of bipolar disorder, seasonal affective disorder. Also depressive symptoms and disorders associated with other psychiatric, neurological or physical medical disorders, examples being, depression associated with schizophrenia, depression associated with dementia, depression associated with physical conditions such as cancer. All anxiety symptoms and disorders including panic disorders, specific phobias, social phobia, social anxiety disorder, post-traumatic stress disorder (PTSD), obsessive-compulsive disorder (OCD), generalized anxiety disorder (GAD). Also anxiety symptoms and disorders associated with other psychiatric, neurological or physical/medical disorders. Also psychiatric syndromes manifested in animals, e.g., horses, cats and dogs.

Compositions comprising essentially pure diastereomer of the present invention are also expected to be an improvement on many existing treatments for bipolar disorder, penile erectile dysfunction (PED), premature ejaculation, eating disorders such as anorexia nervosa (AN), binge disorder and bulimia nervosa (BN), premenstrual dysphoric disorder (PMDD), premenstrual syndrome, pathological gambling, irritable bowel disorder, female sexual dysfunction, inflammatory bowel disease, hot flushes associated with menopause, neuropathic pain, neuralgias, compulsive and obsessive behaviours including pathological shopping disorder, autism, somatic symptoms associated with psychiatric disorders, e.g., non-specific chest pains, fibromyalgia, agitative symptoms. Also treatment of alcohol abuse, smoking and other addictions.

In addition to their use as treatments (first-line or other) for the aforementioned disorders, the compounds of the present invention also hold clinical promise for use in combination therapies in the treatment of human and animal disease. In particular, the present invention provides for combination therapies of an essentially purified diastereomers of 4-aryloxy-3-hydroxypiperidine with other active ingredients. For example, in one embodiment the present invention provides for a combination therapy of an essentially purified diastereomers of 4-aryloxy-3-hydroxypiperidine with desensitisers of the 5-HT1a autoreceptors, such as pindolol. It is contemplated that combination therapies may show a faster onset of antidepressant effects.

The present invention also provides for combination therapies with other active ingredients for the treatment of resistant or refractory depressive, anxiety or bipolar disorders. Such active ingredients include the anti-psychotics, anti-epileptics, other anti-depressants, other anxiolytics, benzodiazepines and mood stabilizers.

The present invention also provides for combination therapies with other antidepressants and/or anxiolytics for the treatment of sub-optimally treated disorders.

In a further embodiment the present invention provides for a method of binding 5-HT receptors in an animal by the administration to an animal of a pharmaceutical composition comprising a compound, wherein the compound is an essentially pure diastereomers of a 4-aryloxy-3-hydroxypiperidines (1) or an addition salt thereof,

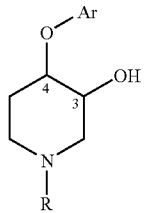

where Ar is a substituted or unsubstituted aromatic hydrocarbon group and R is hydrogen or methyl, carbon 3 is either in the R or the S configuration and carbon 4 is either in the R or the S configuration.

The essentially pure diastereomers of the invention and their pharmaceutically acceptable addition salts possess pharmacological activity as can be shown in standard test methods, and are accordingly indicated for use as pharmaceuticals. The compounds of the present invention have a range of pharmaceutical activities that ensure they will provide a useful addition to the armamentarium of medications available for the treatment of human and animal disease. Their effects are linked, but not always exclusively so, to serotoninergic (also referred to though out this application as 5-HT) functions; their interactions at serotonin receptors show complex behavior in terms of sub-type selectivity, agonist and antagonistic behavior and low and high dose mediated effects.

The selectivity of specific diastereomers of the claimed compounds towards different enzymes and receptors is manifested, for example, in the interaction of isolated essential pure diastereomers of compound 2 with 5-HT receptor sub-types as shown below. As shown below the essentially pure diastereoiosomer of ifoxetine, (3R,4S)-4-(2,3-dimethylphenyl)-3-hydroxypiperidine, is an effective inhibitor of binding to $5\text{-HT}_{1A}$, $5\text{-HT}_{2B}$, and $5\text{-HT}_{2C}$, receptors. It was also found that the essentially pure diastereoiosomer, (3S,4R)-4-(2,3-dimethylphenyl)-3-hydroxypiperidine, inhibits binding to $5\text{-HT}_3$, $5\text{-HT}_{4C}$, and Ne (Norepinephrine) uptake receptors. It was also found that the essentially pure diastereoiosomer, (3S,4S)-4-(2,3-dimethylphenyl)-3-hydroxypiperidine, inhibits binding to $5\text{-HT}_7$, $5\text{-HT}_{2c}$, and Ne uptake receptors. It was also found that the essentially pure diastereoiosomer, (3R,4R)-4-(2,3-dimethylphenyl)-3-hydroxypiperidine, inhibits binding to $5\text{-HT}_{1A}$ and $5\text{-HT}_7$ receptors. The difference in receptor binding between diastereomers of ifoxetine is unexpected in view of the results of Waldmeier, wherein it was disclosed that the racemic ifoxetine had minimal activity at $5\text{-HT}_1$, and $5\text{-HT}_2$ receptors at concentrations of 10 μM of the racemate.

| Assay binding | Compound | % inhibition of control specific at 100 nM conc. |
|---|---|---|
| $5\text{-HT}_{1A}$ | 3S, 4R-4-(2,3-dimethylphenyl)-3-hydroxypiperidine | 9 |
| | 3R, 4S-4-(2,3-dimethylphenyl)-3-hydroxypiperidine | 39 |
| | 3R, 4R-4-(2,3-dimethylphenyl)-3-hydroxypiperidine | 16 |
| | 3S, 4S-4-(2,3-dimethylphenyl)-3-hydroxypiperidine | −8 |
| $5\text{-HT}_{2B}$ | 3S, 4R-4-(2,3-dimethylphenyl)-3-hydroxypiperidine | 6 |
| | 3R, 4S-4-(2,3-dimethylphenyl)-3-hydroxypiperidine | 48 |
| | 3R, 4R-4-(2,3-dimethylphenyl)-3-hydroxypiperidine | 6 |
| | 3S, 4S-4-(2,3-dimethylphenyl)-3-hydroxypiperidine | 6 |
| $5\text{-HT}_3$ | 3S, 4R-4-(2,3-dimethylphenyl)-3-hydroxypiperidine | 11 |
| | 3R, 4S-4-(2,3-dimethylphenyl)-3-hydroxypiperidine | 6 |
| | 3R, 4R-4-(2,3-dimethylphenyl)-3-hydroxypiperidine | 4 |
| | 3S, 4S-4-(2,3-dimethylphenyl)-3-hydroxypiperidine | 5 |
| $5\text{-HT}_{4C}$ | 3S, 4R-4-(2,3-dimethylphenyl)-3-hydroxypiperidine | 15 |
| | 3R, 4S-4-(2,3-dimethylphenyl)-3-hydroxypiperidine | 8 |
| | 3R, 4R-4-(2,3-dimethylphenyl)-3-hydroxypiperidine | 0 |
| | 3S, 4S-4-(2,3-dimethylphenyl)-3-hydroxypiperidine | 5 |
| $5\text{-HT}_7$ | 3S, 4R-4-(2,3-dimethylphenyl)-3-hydroxypiperidine | 6 |
| | 3R, 4S-4-(2,3-dimethylphenyl)-3-hydroxypiperidine | 1 |
| | 3R, 4R-4-(2,3-dimethylphenyl)-3-hydroxypiperidine | 16 |
| | 3S, 4S-4-(2,3-dimethylphenyl)-3-hydroxypiperidine | 22 |
| $5\text{-HT}_{2c}$ | 3S, 4R-4-(2,3-dimethylphenyl)-3-hydroxypiperidine | −17 |
| | 3R, 4S-4-(2,3-dimethylphenyl)-3-hydroxypiperidine | 4 |
| | 3R, 4R-4-(2,3-dimethylphenyl)-3-hydroxypiperidine | −11 |
| | 3S, 4S-4-(2,3-dimethylphenyl)-3-hydroxypiperidine | 7 |
| NE uptake | 3S, 4R-4-(2,3-dimethylphenyl)-3-hydroxypiperidine | 8 |
| | 3R, 4S-4-(2,3-dimethylphenyl)-3-hydroxypiperidine | 3 |
| | 3R, 4R-4-(2,3-dimethylphenyl)-3-hydroxypiperidine | −9 |
| | 3S, 4S-4-(2,3-dimethylphenyl)-3-hydroxypiperidine | 4 |

5-HT receptor binding assays were performed according to the method well known in the art. See for example Mulerhorn et al. J. Biol. Chem. 269 (1994) 12954-12962, Bonhaus et al. (1995) et al. J. Biol. Chem. 269 (1994) 12954-12962 herein incorporated by reference in its entirety. See also U.S. Pat. Nos. 5,126,363; 5,688,807; 5,786,157; and 5,869,691 herein incorporated by reference in their entirety.

Briefly, CHO cells expressing human 5-HT receptor sub-types, or membranes prepared therefrom, were incubated with a specific radioactive ligand for 60 minutes at 22° C. (0.5 nM of [$^3$H]-8-OH-DPAT for $5\text{-HT}_{1A}$ receptors, 1.2 nM of [$^3$H]-LSD for $5\text{-HT}_{2B}$ receptors). Incubations were performed in the presence or absence of one of the following diastereomers: 10 μM 8-OH-DPAT; 100 nM (3S,4R)-4-(2,3-dimethylphenyl)-3-hydroxypiperidine; 100 nM (3R,4S)-4-(2,3-dimethylphenyl)-3-hydroxypiperidine; 100 nM (3R,4R)-4-(2,3-dimethylphenyl)-3-hydroxypiperidine; 100 nM (3S,4S)-4-(2,3-dimethylphenyl)-3-hydroxypiperidine. Following incubation the cells or membranes were washed recovered and the radioactivity content of the filter used to determine specific receptor binding and inhibition by the essential pure diastereomers.

Composition Comprising Essentially Purified Diastereomers of 4-aryloxy-3-hydroxypiperidines In a further embodiment the present invention provides for a pharmaceutical compositions which comprise a pharmaceutically acceptable carrier and an effective amount of an essentially pure diastereomer of a 4-aryloxy-3-hydroxypiperidine (1) or an addition salt thereof,

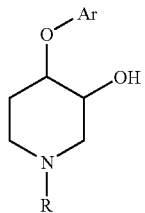

where Ar is a substituted or unsubstituted aromatic hydrocarbon group and R is hydrogen or methyl, carbon 3 is either in the R or the S configuration and carbon 4 is either in the R or the S configuration and a pharmaceutically acceptable carrier.

As used herein, an effective amount of an essentially pure diastereomer may refer to low dosages for some disorders and high dosages for other disorders. Preferably, an effective amount refers to a dosage of about 0.1 mg to about 800 mg.

Preferably, the composition is administered about 1 to about 4 times a day. More preferably, the composition is administered about 1 to about 2 times a day. Most preferably, the composition is administered once a day.

In a further embodiment the present invention provides for a pharmaceutical composition comprising essentially pure (3R,4S), -4-(2,3-dimethylphenyl)-3-hydroxypiperidine or an addition salt thereof and a pharmaceutically acceptable carrier.

In a further embodiment the present invention provides for a pharmaceutical composition comprising essentially pure (3S,4R), -4-(2,3-dimethylphenyl)-3-hydroxypiperidine or an addition salt thereof and a pharmaceutically acceptable carrier.

In a further embodiment the present invention provides for a pharmaceutical composition comprising essentially pure (3R,4R)-4-(2,3-dimethylphenyl)-3-hydroxypiperidine or an addition salt thereof and a pharmaceutically acceptable carrier.

In a further embodiment the present invention provides for a pharmaceutical composition comprising essentially pure (3S,4S)-4-(2,3-dimethylphenyl)-3-hydroxypiperidine or an addition salt thereof and a pharmaceutically acceptable carrier.

It is provided that the essentially purified diastereomers of 4-aryloxy-3-hydroxypiperidines of the invention may be administered as a purified compound. Preferably, however, the essentially purified diastereomer of 4-aryloxy-3-hydroxypiperidine will be administered as a pharmaceutical composition with a pharmaceutically acceptable carrier. It is provided that the essentially purified diastereomer of 4-aryloxy-3-hydroxypiperidines of the invention may be administered in any suitable manner, for example, in the form of a tablet, capsule, liquid (e.g. syrup) or by injection, including orally, parenterally (including subcutaneously, intramuscularly and intravenously), or topically.

The present invention provides for a pharmaceutical composition comprising a pharmaceutically acceptable carrier and, as an active ingredient, an effective amount of an essentially purified diastereomer of 4-aryloxy-3-hydroxypiperidines of compound 1 or pharmaceutically acceptable salt thereof. Preferably the essentially purified diastereomer is a diastereomer of compounds 2 to 5 or pharmaceutically acceptable salt thereof. Most preferably the essentially purified diastereomer is (3R,4S)-4-(2,3-dimethylphenyl)-3-hydroxypiperidine, (3S,4R), -4-(2,3-dimethylphenyl)-3-hydroxypiperidine, (3R,4R)-4-(2,3-dimethylphenyl)-3-hydroxypiperidine, or (3S,4S)-4-(2,3-dimethylphenyl)-3-hydroxypiperidine.

The effective amount of essentially purified diastereomers of 4-aryloxy-3-hydroxypiperidines will of course vary and is ultimately at the discretion of the medical or veterinary practitioner in each particular case. The factors to be considered by such a practitioner, e.g. a physician, include the route of administration and pharmaceutical formulation; the subject's body weight, surface area, age and general condition; and the chemical form of the compound to be administered.

It is contemplated that the essentially purified diastereomers of 4-aryloxy-3-hydroxypiperidines may be given as a single dose, multiple doses, or by intravenous infusion for any selected duration.

The essentially purified diastereomers of the 4-aryloxy-3-hydroxypiperidine may be formulated into a variety of pharmaceutical compositions and dosage forms that are useful in treating patients.

Pharmaceutical compositions of the present invention contain the essentially purified diastereomer of the 4-aryloxy-3-hydroxypiperidine as an active ingredient. In addition to the active ingredient(s), the pharmaceutical compositions of the present invention may contain one or more excipients. Excipients are added to the composition for a variety of purposes.

Diluents increase the bulk of a solid pharmaceutical composition and may make a pharmaceutical dosage form containing the composition easier for the patient and caregiver to handle. Diluents for solid compositions include, for example, microcrystalline cellulose (e.g. AVICEL7, microfine cellulose, lactose, starch, pregelitinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g. Eudragit7), potassium chloride, powdered cellulose, sodium chloride, sorbitol and talc.

Solid pharmaceutical compositions that are compacted into a dosage form like a tablet may include excipients whose functions include helping to bind the active ingredient and other excipients together after compression. Binders for solid pharmaceutical compositions include acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. KLUCEL7), hydroxypropyl methyl cellulose (e.g. METHOCEL7), liquid glucose, magnesium aluminum silicate, maltodextrin, methylcellulose, polymethacrylates, povidone (e.g. KOLLIDON7, PLASDONE7), pregelatinized starch, sodium alginate and starch.

The dissolution rate of a compacted solid pharmaceutical composition in the patient's stomach may be increased by the addition of a disintegrant to the composition. Disintegrants include alginic acid, carboxymethylcellulose calcium, carboxymethylcellulose sodium (e.g. Ac-DI-SOL7, PRIMELOSE7), colloidal silicon dioxide, croscarmellose sodium, crospovidone (e.g. KOLLIDON7, POLYPLASDONE7), guar gum, magnesium aluminum silicate, methyl cellulose, microcrystalline cellulose, polacrilin potassium, powdered cellulose, pregelatinized starch, sodium alginate, sodium starch glycolate (e.g. EXPLOTAB7) and starch.

Glidants can be added to improve the flow properties of non-compacted solid compositions and improve the accuracy of dosing. Excipients that may function as glidants include colloidal silicon dixoide, magnesium trisilicate, powdered cellulose, starch, talc and tribasic calcium phosphate.

When a dosage form such as a tablet is made by compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion and ease release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl famarate, stearic acid, talc and zinc stearate.

Flavoring agents and flavor enhancers make the dosage form more palatable to the patient. Common flavoring agents and flavor enhancers for pharmaceutical products that may be included in the composition of the present invention include maltol, vanillin, ethyl vanillin, menthol, citric acid, fumaric acid ethyl maltol, and tartaric acid.

Compositions may also be colored using any pharmaceutically acceptable colorant to improve their appearance and/or facilitate patient identification of the product and unit dosage level.

Selection of excipients and the amounts to use may be readily determined by the formulation scientist based upon experience and consideration of standard procedures and reference work in the field.

The solid compositions of the present invention include powders, granulates, aggregates and compacted compositions. The dosages include dosages suitable for oral, buccal, sublingual rectal, parenteral (including subcutaneous, intramuscular, and intravenous), inhalant and ophthalmic administration also and via nasal spray. Although the most suitable route in any given case will depend on the nature and severity of the condition being treated, the most preferred route of the present invention is oral. The dosages may be conveniently presented in unit dosage form and prepared by any of the methods well-known in the pharmaceutical arts.

Dosage forms include solid dosage forms like tablets, powders, capsules, suppositories, sachets, troches, fast dissolving preparations and lozenges as well as liquid syrups, suspensions and elixirs. An especially preferred dosage form of the present invention is a tablet.

Such pharmaceutical compositions for medical use will be formulated in accordance with any of the methods well known in the art of pharmacy for administration in any convenient manner. The compounds of the invention will usually be admixed with at least one other ingredient providing a compatible pharmaceutically acceptable additive, carrier, diluent or excipient, and may be presented in unit dosage form.

The carrier(s) must be pharmaceutically acceptable in the sense of being compatible with the other ingredients of the formulation and not deleterious to the recipient thereof.

The possible formulations include those suitable for oral, rectal, topical and parenteral (including subcutaneous, intramuscular and intravenous) administration or for administration to the lung or another absorptive site such as the nasal passages.

All methods of formulation in making up such pharmaceutical compositions will generally include the step of bringing the diastereomer of compounds 2 to 5 into association with a carrier which constitutes one or more accessory ingredients. Usually, the formulations are prepared by uniformly and intimately bringing the essentially purified diastereomer of compounds 2 to 5 into association with a liquid carrier or with a finely divided solid carrier or with both and then, if necessary, shaping the product into desired formulations.

Formulations of the present invention suitable for oral administration may be presented as discrete units such as capsules, cachets, tablets or lozenges, each containing a predetermined amount of the essentially purified diastereomer of compounds 2 to 5; as a powder or granules; or a suspension in an aqueous liquid or non-aqueous liquid such as a syrup, an elixir, an emulsion or a draught. The essentially purified diastereomer of compounds 2 to 5 may also be presented as a bolus, electuary or paste.

A tablet may be made by compression or moulding, optionally with one or more accessory ingredients. Compressed tablets may be prepared by compressing, in a suitable machine, the essentially purified diastereomer of compounds 2 to 5 in a free-flowing form such as a powder or granules, optionally mixed with a binder, lubricant, inert diluent, surface active or dispersing agent. Moulded tablets may be made by moulding, in a suitable machine, a mixture of the powdered essentially purified diastereomer of compounds 2 to 5 with any suitable carrier.

A syrup may be made by adding the essentially purified diastereomer of compounds 2 to 5 to a concentrated, aqueous solution of a sugar, for example sucrose, to which may be added any desired accessory ingredient. Such accessory ingredient(s) may include flavourings, an agent to retard crystallisation of the sugar or an agent to increase the solubility of any other ingredient, such as a polyhydric alcohol, for example glycerol or sorbitol.

Formulations for rectal administration may be presented as a suppository with a usual carrier such as cocoa butter.

Formulations suitable for parental administration conveniently comprise a sterile aqueous preparation of the essentially purified diastereomer of compounds 2 to 5 which is preferably isotonic with the blood of the recipient.

In addition to the aforementioned ingredients, formulations of this invention, for example ointments, creams and the like, may include one or more accessory ingredients, for example a diluent, buffer, flavouring agent, binder, surface active agent, thickener, lubricant and/or a preservative (including an antioxidant) or other pharmaceutically inert excipient.

The compounds of this invention may also administered as a liposomal formulation which can be prepared by methods well-known in the art. See for example U.S. Pat. Nos. 5,446,070, 5,891,465, 5,759,573, 5,997,899, and 5,962,016, each of which is incorporated by reference in its entirety.

The function and advantage of these and other embodiments of the present invention will be more fully understood from the examples below. The following examples are intended to illustrate the benefits of the present invention, but do not exemplify the full scope of the invention.

EXAMPLES

Example 1

Preparation 1 of trans-racemic 4-(2,3-dimethylphenoxy)-3-hydroxypiperidine

Step 1. A stirred solution of benzyl 3,6-dihydropyridine-1 (2H)-carboxylate (20.0 g, 92.0 mmol) in dichloromethane (280 ml) was cooled to 0° C. A solution of m-chloroperoxybenzoic acid (22.5 g, approx. 130 mmol) in dichloromethane (560 ml) was added drop-wise and the resulting colourless reaction mixture warmed to room temperature. After an additional 4 h at room temperature (reaction complete by tlc using 50:50 hexane:ethyl acetate as eluent.) the reaction mixture was washed with aqueous potassium carbonate solution (5 wt %, 3×200 ml) and brine (200 ml). The organic layer was dried over anhydrous magnesium sulfate, filtered and concentrated in vacuo to furnish benzyl 7-oxa-3-azabicyclo[4.1.0]heptane-3-carboxylate as a yellow oil (22.0 g; 100%).

Step 2. Benzyl 7-oxa-3-azabicyclo[4.1.0]heptane-3-carboxylate (21.0 g, 92.0 mmol) was added to a stirred solution of 2,3-dimethylphenol (23.0 g, 188 mmol) and aqueous sodium hydroxide (100 ml, 2N, 200 mmol) in acetonitrile (400 ml). The reaction mixture was heated at reflux for 14 h. On cooling to room temperature, the reaction mixture was concentrated in vacuo before dilution with water (500 ml). Extraction with dichloromethane (4×100 ml) was followed by washing of the combined organics with aqueous sodium hydroxide (100 ml, 3N, 300 mmol), water (100 ml) and brine (100 ml). The organics were dried over anhydrous magnesium sulfate, filtered and concentrated in vacuo to furnish a crude product. Purification was carried out by silica gel chromatography using a gradient eluent system of iso-hexanes and ethyl acetate (100% iso-hexanes to 80:20 iso-hexanes: ethyl acetate) to furnish trans-benzyl-4-(2,3-dimethylphenoxy)-3-hydroxypiperidine-1-carboxylate as a pale yellow syrup (16.8 g, 50%).

Step 3. A solution of trans-benzyl 4-(2,3-dimethylphenoxy)-3-hydroxypiperidine-1-carboxylate (3.5 g, 9.8 mmol) in methanol (50 ml) was added to 5% palladium on charcoal (350 mg) under an atmosphere of nitrogen. The vessel was placed under an atmosphere of hydrogen and stirred vigorously until hydrogen uptake ceased. The resulting suspension was filtered over a short pad of celite (pre-washed with methanol) and the pad washed with a further portion of methanol (100 ml). Concentration of the methanolic solution in vacuo gave a yellow oil. Dilution with diethyl ether (100 ml) yielded trans-4-(2,3-dimethylphenoxy)-3-hydroxypiperidine as a white solid (1.01 g, 50%).

Example 2

Preparation 2 of cis-racemic 4-(2,3-dimethylphenoxy)-3-hydroxypiperidine

Step 1. A solution of oxalyl chloride (3.5 ml, 40 mmol, 1.1 eq.) in dichloromethane (350 ml) was cooled to −60° C. (internal temp.) and treated drop-wise with dimethyl sulfoxide (5.18 ml, 73.0 mmol, 2 eq.). On completion of addition the reaction mixture was stirred at −60° C. for 5 min. before drop-wise addition of a solution of trans-benzyl-4-(2,3-dimethylphenoxy)-3-hydroxypiperidine-1-carboxylate (13.0 g, 36.5 mmol) in dichloromethane (50 ml). After 30 min. triethylamine (15.5 ml, 110 mmol, 3.0 eq.) was added drop-wise and the solution stirred at −60° C. for 10 min, before allowing the mixture to warm slowly to room temperature. After 18 h. the reaction mixture was diluted with water (400 ml) and the resultant biphasic system separated. The aqueous layer was extracted with dichloromethane (400 ml). Combined organics were washed with aqueous hydrochloric acid (200 ml, 0.1N), dried over anhydrous magnesium sulfate, filtered and concentrated in vacuo to furnish benzyl 4-(2,3-dimethylphenoxy)-3-oxopiperidine-1-carboxylate as a pale yellow amorphous solid (12.8 g, 99%).

Step 2. A solution of benzyl 4-(2,3-dimethylphenoxy)-3-oxopiperidine-1-carboxylate (10.0 g, 28.0 mmol) in tetrahydrofuran (60 ml) was treated at room temperature with K-selectride (10.0M in tetrahydrofuran, 56 ml, 56.0 mmol). On completion of addition the mixture was stirred at room temperature for 18 h. The mixture was concentrated to dryness in vacuo and diluted carefully by addition of ice-water (100 ml). Extraction with dichloromethane (2×200 ml) was followed by washing the combined organics with aqueous hydrochloric acid (100 ml, 0.1N), water (100 ml) and brine (100 ml). The organics were dried over anhydrous magnesium sulfate, filtered and concentrated in vacuo to give a dark oil which was purified by silica gel chromatography using isohexanes:ethyl acetate (5:1) as eluent to furnish cis-benzyl 4-(2,3-dimethylphenoxy)-3-hydroxypiperidine-1-carboxylate as a pale yellow syrup (5.01 g, 50%).

Step 3. A solution of cis-benzyl 4-(2,3-dimethylphenoxy)-3-hydroxypiperidine-1-carboxylate (5.0 g, 14.0 mmol) in methanol (60 ml) was added to 5% palladium on charcoal (500 mg) under an atmosphere of nitrogen. The vessel was placed under an atmosphere of hydrogen and stirred vigorously until hydrogen uptake ceased. The resulting suspension was filtered over a short pad of celite (pre-washed with methanol) and the pad washed with a further portion of methanol (150 ml). Concentration of the methanolic solution in vacuo gave a yellow oil. Dilution with diethyl ether (150 ml) yielded cis-4-(2,3-dimethylphenoxy)-3-hydroxypiperidine as a white solid (2.1 g, 67%).

Example 3

Purification of Stereoisomers of 4-(2,3-dimethylphenoxy)-3-hydroxypiperidine

A solution of cis 4-(2,3-dimethylphenoxy)-3-hydroxypiperidine was prepared at a concentration of 0.5 mg/ml in HPLC grade ethanol; sonication for at least 10 min was required to ensure complete dissolution. Separation was carried out using the following parameters:

| | |
|---|---|
| Column | Chiralpak AD 250 × 4.6 mm 5μ |
| Column Temperature | ambient |
| Flow | 0.5 ml/min |
| Injection Volume | 10 μl |
| Wavelength Range | 254 nm |
| Mobile Phase | HPLC ethanol |
| Run time | 20 min |

The procedure was repeated for trans-(2,3-dimethylphenoxy)-3-hydroxypiperidine. The trans isomer required sonication for 10 minutes prior to HPLC purification.

Retention times were as follows: 3S, 4R-4-(2,3-dimethylphenyl)-3-hydroxypiperidine, 8.3 minutes; 3R, 4S-4-(2,3-dimethylphenyl)-3-hydroxypiperidine, 10.7 minutes; 3R, 4R-4-(2,3-dimethylphenyl)-3-hydroxypiperidine, 8.9 minutes; and nM 3S, 4S-4-(2,3-dimethylphenyl)-3-hydroxypiperidine, 10.7 minutes. The identification of each compound was made by optical rotation.

Example 4

Preperative Purification of Stereoisomers of 4-(2,3-dimethylphenoxy)-3-hydroxypiperidine A solution of cis 4-(2,3-dimethylphenoxy)-3-hydroxypiperidine was prepared at a concentration of 0.5 mg/ml in HPLC grade ethanol; sonication for at least 10 min was required to ensure complete dissolution. Separation was carried out using the following parameters:

| | |
|---|---|
| Column | Chiralpak AD 250 × 20.00 mm 10μ |
| Column Temperature | ambient |
| Flow | 5 ml/min |
| Injection Volume | 1000 μl |
| Wavelength Range | 254 nm |
| Mobile Phase | HPLC ethanol |
| Run time | 20 min. (please confirm) |
| Wash Solvent | Hexane/IPA 90:10 |

The procedure was repeated for trans-(2,3-dimethylphenoxy)-3-hydroxypiperidine. The trans isomer required sonication for 10 minutes prior to HPLC purification.

Retention times were as follows: (3S,4R)-4-(2,3-dimethylphenyl)-3-hydroxypiperidine, 14.5 minutes; (3R,4S)-4-(2,3-dimethylphenyl)-3-hydroxypiperidine, 16.5 minutes; (3R,4R)-4-(2,3-dimethylphenyl)-3-hydroxypiperidine, 15 minutes; and nM (3S,4S)-4-(2,3-dimethylphenyl)-3-hydroxypiperidine, 17 minutes. The identification of each compound was made by optical rotation.

What is claimed is:

1. An essentially pure diastereomer of a 4-aryloxy-3-hydroxypiperidine (1) or an addition salt thereof,

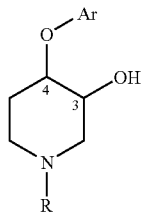

1 wherein the diastereomer is in the (3R,4S) configuration, Ar is selected from a group consisting of 2,3-dimethylphenyl and 3,4-dimethylphenyl, R is selected from a group consisting of hydrogen and methyl, and the diastereomer is greater than about 90% purified from other isomers of formula 1.

2. The diastereomer of claim 1, wherein the diastereomer is greater than about 95% purified from other isomers of formula 1.

3. The diastereomer of claim 1, wherein the diastereomer is greater than about 98% purified from other isomers of formula 1.

4. An essentially pure diastereomer of 4-(2,3-dimethylphenyl)-3-hydroxypiperidine or an addition salt thereof, wherein the diastereomer is (3R,4S)-4-(2,3-dimethylphenyl)-3-hydroxypiperidine, and the diastereomer is greater than about 90% purified from other isomers of 4-(2,3-dimethylphenyl)-3-hydroxypiperidine.

5. The diastereomer of claim 4, wherein the diastereomer is greater than about 95% purified from other isomers of 4-(2,3-dimethylphenyl)-3-hydroxypiperidine.

6. The diastereomer of claim 4, wherein the diastereomer is greater than about 98% purified from other isomers of 4-(2,3-dimethylphenyl)-3-hydroxypiperidine.

7. A pharmaceutical composition, comprising a pharmaceutically acceptable carrier and an effective amount of an essentially pure diastereomer of a 4-aryloxy-3-hydroxypiperidine (1) or an addition salt thereof.

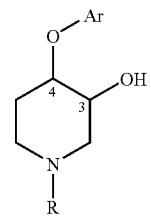

1 wherein the diastereomer is in the (3R,4S) configuration, Ar is selected from a group consisting of 2,3-dimethylphenyl and 3,4-dimethylphenyl, R is selected from a group consisting of hydrogen and methyl, and the diastereomer is greater than about 90% purified from other isomers of formula 1.

8. The diastereomer of claim 7, wherein the diastereomer is greater than about 95% purified from other isomers of formula 1.

9. The diastereomer of claim 7, wherein the diastereomer is greater than about 98% purified from other isomers of formula 1.

10. The pharmaceutical composition of claim 7, wherein the composition is in a form for administration as a tablet, a capsule, a liquid or an injection.

11. A pharmaceutical composition, comprising a pharmaceutically acceptable carrier and an effective amount of an essentially pure diastereomer of 4-(2,3-dimethylphenyl)-3-hydroxypiperidine or an addition salt thereof, wherein the diastereomer is (3R,4S)-4-(2,3-dimethylphenyl)-3-hydroxypiperidine, and the diastereomer is greater than about 90% purified from other isomers of 4-(2,3dimethylphenyl)-3-hydroxypiperidine.

12. The diastereomer of claim 11, wherein the diastereomer is greater than about 95% purified from other isomers of 4-(2,3-dimethylphenyl)-3-hydroxypiperidine.

13. The diastereomer of claim 11, wherein the diastereomer is greater than about 98% purified from other isomers of 4-(2,3-dimethylphenyl)-3-hydroxypiperidine.

14. The pharmaceutical composition of claim 11, wherein the composition is in a form for administration as a tablet, a capsule, a liquid or an injection.

* * * * *

UNITED STATES PATENT AND TRADEMARK OFFICE
CERTIFICATE OF CORRECTION

PATENT NO.       : 7,504,419 B2                                                Page 1 of 1
APPLICATION NO.  : 10/932857
DATED            : March 17, 2009
INVENTOR(S)      : Balvinder Singh Rattan It is certified that error appears in the above-identified patent and that said Letters Patent is hereby corrected as shown below:

Column 10, line 49, change "5-HT1a" to -- $5\text{-HT}_{1a}$ --;

Column 13, line 35, change "(3R,4S), -4-(2,3-dimethylphenyl)-3-hydroxypiperdine" to -- (3R,4S) -4-(2,3-dimethylphenyl)-3-hydroxypiperdine --;

Column 13, line 40, change "(3S,4R), -4-(2,3-dimethylphenyl)-3-hydroxypiperdine" to -- (3S,4R) -4-(2,3-dimethylphenyl)-3-hydroxypiperdine --;

Column 14, line 8, change "(3S,4R), -4-(2,3-dimethylphenyl)-3-hydroxypiperdine" to -- (3S,4R) -4-(2,3-dimethylphenyl)-3-hydroxypiperdine --;

Column 17, line 14, change "by tlc" to -- by TLC --;

Signed and Sealed this

Nineteenth Day of May, 2009

JOHN DOLL
*Acting Director of the United States Patent and Trademark Office*